United States Patent [19]
Moerk et al.

[11] Patent Number: 5,861,755
[45] Date of Patent: Jan. 19, 1999

[54] TWO-PHASE QUALITY/FLOW METER

[75] Inventors: J. Steven Moerk, Taylorsville, N.C.; Robert C. Youngquist, Cocoa; Rudy J. Werlink, Winter Springs, both of Fla.

[73] Assignee: The United States of America as represented by the Adminstrator of National Aeronautics and Space Administration, Washington, D.C.

[21] Appl. No.: 552,456

[22] Filed: Nov. 6, 1995

[51] Int. Cl.⁶ .................................................. G01N 27/22
[52] U.S. Cl. ........................ 324/663; 324/678; 324/690; 73/861.04; 73/19.1
[58] Field of Search ...................... 324/663, 664, 324/667, 674–678, 686, 690; 73/861.04, 19.1, 861.08

[56] References Cited

U.S. PATENT DOCUMENTS

| | | | |
|---|---|---|---|
| 3,006,189 | 10/1961 | Warren et al. | 73/861.04 |
| 3,067,385 | 12/1962 | Rykoskey | 324/663 |
| 3,523,245 | 8/1970 | Love | 324/686 |
| 3,595,078 | 7/1971 | Beck | 73/861.04 |
| 3,635,082 | 1/1972 | Prellwitz et al. | 73/861.04 |
| 3,748,446 | 7/1973 | Gass et al. | 364/57.3 |
| 3,761,805 | 9/1973 | Dornberger | 324/678 |
| 4,020,690 | 5/1977 | Samuels et al. | 73/299 |
| 4,103,225 | 7/1978 | Stephens | 324/678 |
| 4,509,366 | 4/1985 | Matsushita et al. | 73/861.02 |
| 4,713,603 | 12/1987 | Thorn | 324/688 |
| 4,825,147 | 4/1989 | Cook et al. | 324/678 |
| 4,835,456 | 5/1989 | Liu et al. | 324/674 |
| 4,975,645 | 12/1990 | Lucas | 324/324 |
| 5,005,402 | 4/1991 | Pischinger et al. | 324/663 |
| 5,051,922 | 9/1991 | Toral et al. | 364/510 |
| 5,274,334 | 12/1993 | Mills | 324/678 |
| 5,291,791 | 3/1994 | Lucas et al. | 73/861.08 |
| 5,396,806 | 3/1995 | Dechene et al. | 73/861.04 |
| 5,576,628 | 11/1996 | Caliboso et al. | 324/678 |
| 5,585,733 | 12/1996 | Paglione | 324/678 |

FOREIGN PATENT DOCUMENTS

| 0104243 | 8/1981 | Japan | 324/663 |
|---|---|---|---|

OTHER PUBLICATIONS

Mahmud et al., "A Microprocesor–Based Switched Battery Capacitance Meter", IEEE Transactions on Instrumentation and Measurement, vol. 37, No. 2, Jun. 1988.

*Primary Examiner*—Michael Brock
*Attorney, Agent, or Firm*—Beth A. Vrioni

[57] ABSTRACT

A quality and/or flow meter employs a capacitance probe assembly for measuring the dielectric constant of flow stream, particularly a two-phase flow stream including liquid and gas components. The dielectric constant of the flow stream varies depending upon the volume ratios of its liquid and gas components, and capacitance measurements can therefore be employed to calculate the quality of the flow, which is defined as the volume ratio of liquid in the flow to the total volume ratio of gas and liquid in the flow. By using two spaced capacitance sensors, and cross-correlating the time varying capacitance values of each, the velocity of the flow stream can also be determined. A microcontroller-based processing circuit is employed to measure the capacitance of the probe sensors. The circuit employs high speed timer and counter circuits to provide a high resolution measurement of the time interval required to charge each capacitor in the probe assembly. In this manner, a high resolution, noise resistant, digital representation of each of capacitance value is obtained without the need for a high resolution A/D converter, or a high frequency oscillator circuit. One embodiment of the probe assembly employs a capacitor with two ground plates which provide symmetry to insure that accurate measurements are made thereby.

8 Claims, 4 Drawing Sheets

TWO-PHASE QUALITY/FLOW METER

ORIGIN OF THE INVENTION

The invention described herein was made in the performance of work under a NASA contract, and is subject to the provisions of Public Law 96–517 (94 Stat. 3019; 35 USC 200–211).

BACKGROUND OF THE INVENTION

The present invention relates in general to a two-phase quality/flow meter which can measure the ratio of liquid to gas in, and the flow velocity of, a two-phase flow stream by using capacitance measurements.

Many prior art measurement devices monitor capacitance changes to measure a physical phenomenon related thereto. For example, because different materials typically have different dielectric constants, a capacitance measurement performed on a mixture of two materials can be employed to determine the ratio of one material to the other. Similarly, the dielectric constant of a single material typically changes when the material changes phase between a liquid and a gas or a liquid and a solid. Thus, the ratio of one phase to another phase in a two-phase flow stream can also be determined using capacitance measurements. This measurement technique is useful in "quality" meters which measure the volume ratio of a gas or liquid component in gas-liquid mixture to the total volume of the mixture, where quality is defined as this ratio. A specific application of a quality meter is in the monitoring of a cryogenic flow of liquid nitrogen, hydrogen or oxygen as is typically used for fueling rocket engines. Cryogenic cooling is required to maintain these elements in their liquid state due to their very low boiling temperatures. Even the slightest malfunction in the cryogenic cooling system can result in the generation of gas bubbles in the flow stream, and these can be very detrimental to the proper operation of the fuel supply system. Accordingly, a means must be provided which can rapidly detect when the proportion of liquid volume to the total volume in the flow stream drops below an unacceptable level, and quality meters provide an accurate means for monitoring such a condition.

Capacitance measurements can also be employed to measure the flow velocity of a material flow stream by making capacitance measurements with two capacitance sensors disposed at spaced locations in the flow stream, and cross-correlating the obtained measurements. The cross-correlation determines when like portions of the flow stream pass each capacitance sensor, and the flow velocity can be determined by dividing the distance between the two sensors by the time interval required for like portions of the flow to pass from one sensor to the other.

Prior art capacitance based measurement devices of these type suffer from a number of drawbacks. Typically, these devices employ a capacitance probe which is positioned in the flow or material to be tested. The probe includes two spaced conductive plates which form the capacitor, and the material to be tested forms the dielectric between the plates. Thus, if the material's dielectric constant changes, such as may occur as a result of a partial phase change, the value of the capacitor also changes.

Numerous techniques have been employed to measure the capacitance of the capacitor in these devices. In a first known technique, the capacitor is connected as part of an RC oscillator circuit whose frequency changes in proportion to changes in the capacitor's dielectric constant. Although this frequency monitoring technique has the benefit of simple electronics, it has the detriment of requiring that a division be performed, which is difficult with analog circuitry. Additionally, this type of device typically employs a high frequency oscillator which is very sensitive to electrical noise induced errors. Further, temperature and pressure changes affect the device capacitance, and these parameters are thus also a source of error.

Another prior art capacitance measurement technique employs a high frequency oscillator to rapidly charge and discharge the capacitor, and the current required to do this is measured. If the capacitor changes in value, a differing amount of current will be required to charge and discharge it. This technique allows high speed monitoring of the capacitance value, but has the detriments of requiring a high speed, accurate and stable oscillator, voltage-to-current monitoring at high speed, and an accurate, high resolution analog to digital converter. Again, the high frequency oscillator is very sensitive to electrical induced errors, and its stability is affected by various factors, such as temperature and pressure changes. Also, the high resolution analog to digital converter increases both the device complexity and its cost.

SUMMARY OF THE INVENTION

The present invention seeks to overcome the drawbacks of prior art capacitance based quality meters and flow meters by providing such a device which eliminates the need for a high frequency oscillator circuit to measure capacitance changes. Instead, the invention employs circuitry which accurately measures the time required to charge a probe capacitor to a threshold voltage. Timer and counter circuits are employed to measure the elapsed time between the start of capacitor charging and the attainment of the threshold value, resulting in a digital value which is fed directly into a microprocessor, and is linearly proportional to the capacitance value.

The beauty of this arrangement is that it effectively generates a high resolution digital value based upon analog measurements without use of an expensive, high resolution analog to digital converter. In addition, this arrangement is extremely noise tolerant since it does not rely upon frequency changes to convert a capacitance measurement to a digital value. The only frequency sensitive components employed in the device are the clocks for driving the timer and counter circuits and the microprocessor, however, variations in the clock frequency have no effect on the charging interval measurement made by the timer circuit. By employing a very high frequency clock, a short charging interval can be selected which enables a capacitance measurement to be made by the present invention in as little as one millisecond. Thus, the present invention is particularly useful in applications which require very fast response times, such as for example, cryogenic liquid fuel supply systems, which must be able to detect gas bubbles in the flow stream very quickly.

The present invention also employs capacitive probe structures which further increase the accuracy of the quality and flow measurements obtained with the present invention. A first preferred embodiment of the structure employs a long probe body which is split at its center to provide two separate, spaced probes for making the capacitance measurements. A flow directing tube surrounds the probes which has an increased diameter along the probe body length to maintain the flow cross-section constant around the probes. The two probes and the flow directing tube combine to form first and second coaxial measurement capacitors, with the exterior surfaces of the probes forming a center plate for each measurement capacitor, and the inner surface of the flow directing tube forming the outer, ground plate for each measurement capacitor.

The probe structure also incorporates a number of additional features including a vacuum jacket, which surrounds the flow directing tube, and is employed to minimize heat losses. Temperature and pressure sensors are also incorporated in the probe assembly for generating signals that can be used to compensate for pressure and temperature induced measurement errors. Finally, the symmetry of the device enables it to be employed for measuring flows in two directions.

In a second preferred embodiment of the capacitive probe structure, the probe assembly employs first, second and third spaced plates which are positioned in the flow directing tube with their longitudinal axes parallel to the flow stream. The center plate forms a first plate for the measurement capacitor, while the outer plates are grounded to one another, and thus form the second plate of the capacitor. The two ground plates are employed to insure that the curvature of the flow directing tube will not influence the measurements in a non-symmetrical manner since the flow directing tube is also at ground potential.

BRIEF DESCRIPTION OF THE DRAWINGS

These and other features and advantages of the present invention will become apparent from the following detailed description of a number of preferred embodiments thereof, taken in conjunction with the accompanying drawings, in which.

DETAILED DESCRIPTION OF THE PREFERRED EMBODIMENTS

Figure 1:
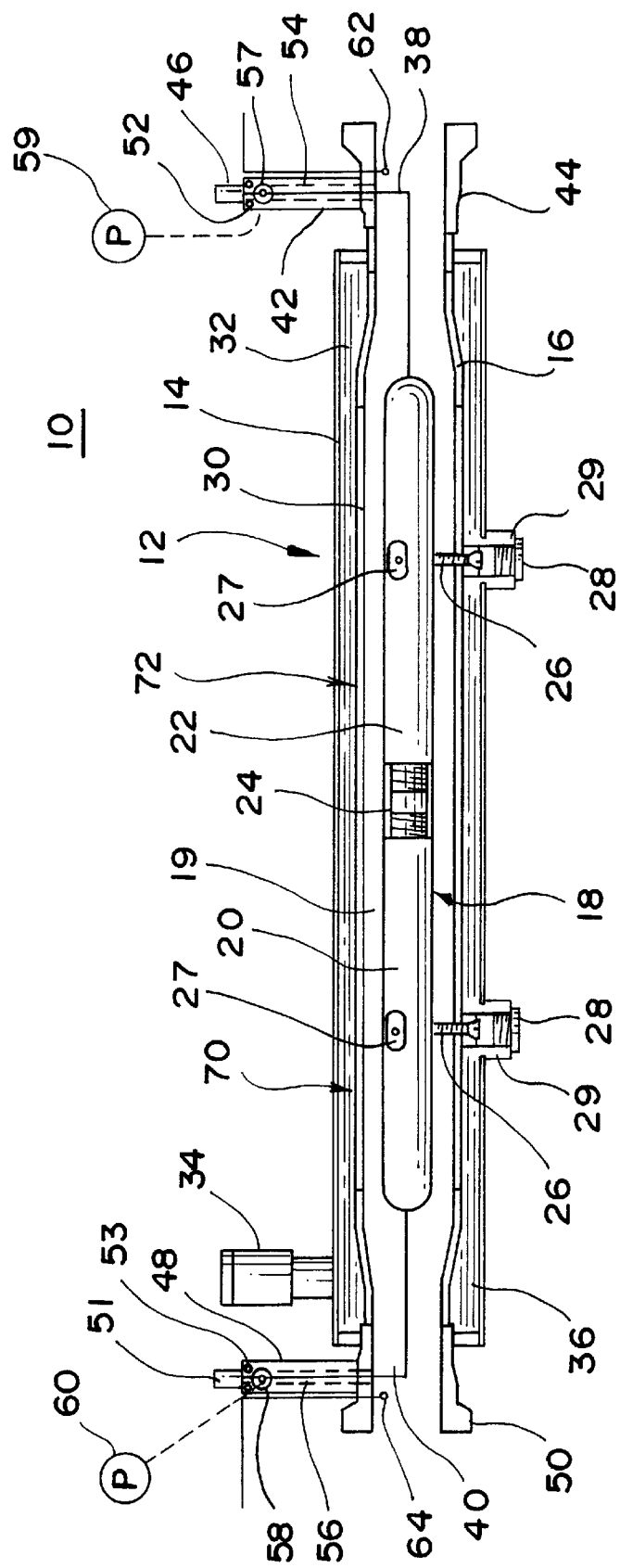
FIG. 1 is a cut-away front elevation of a first embodiment of a capacitance probe assembly for obtaining quality and flow measurements of a material flow stream.

Turning now to FIG. 1, a first preferred embodiment of a capacitance probe assembly 10 is illustrated for insertion into a two-phase flow stream to be monitored. The assembly 10 includes a tubular housing 12 comprised of an outer, vacuum jacket 14 and an inner, flow directing tube 16.

Centrally disposed within the inner, flow directing tube 16 is an elongated probe body 18. A flow passage 19 is defined by the flow directing tube 16 which surrounds the probe body 18. The probe body 18 is separated into first and second spaced probes 20 and 22 by means of a threaded sleeve spacer 24 that is made out of an insulating (e.g., phenolic) material. A plurality of radially spaced screws 26 supports the probe body 18 within the flow directing tube 16. Each of these is screwed into corresponding ones of a plurality of electrically insulating pads 27 that are equally spaced (e.g. every 120°) around the periphery of each of the probes 20 and 22. Preferably, the pads 27 are also formed from phenolic material. A plurality of threaded plugs 28 are secured in a plurality of corresponding apertures 29 in the outer, vacuum jacket 14. The plugs 28 are removable to provide access to the screws 26 so that the probe body 18 can be removed from the probe assembly 10 as necessary for replacement or repair.

To insure that the velocity of the flow stream passing through the probe assembly 10 is maintained constant, the inner diameter of the flow directing tube 16 is increased along a center section 30 thereof where the tube 16 surrounds the probe body 18. The cross sectional area of the flow passage 19 is therefore constant throughout the length of the probe assembly 10, in spite of the presence of the probe body 18 in the tube 16. This minimizes pressure drop effects along the length of the flow directing tube 16 which could create measurement errors.

A sealed space 32 is formed between the outer vacuum jacket 14 and the inner, flow directing tube 16, and a vacuum is preferably maintained therein by means of a vacuum source (not shown) which is connected to a vacuum valve/fill port 34 at one end of the jacket 14. The sealed space 32 minimizes heat losses, and these can be further minimized by filling the space 32 with a plurality of layers 36 of thermal radiant barrier material, such as aluminized mylar. This is particularly important when the probe assembly 10 is employed in applications requiring measurements to be made on cryogenically cooled flow streams.

First and second electrical wires 38 and 40 are attached to the probes 20 and 22, respectively, for electrically connecting them to a processing circuit illustrated in FIGS. 3 and 4, and discussed below. The first wire 38 passes through a first standoff 42 which is disposed at a first end 44 of the flow directing tube 16, and terminates at a first electrical connector 46 mounted on top of the standoff 42. Similarly, the second wire 40 passes through a second standoff 48 which is disposed at a second end 50 of the flow directing tube 16, and terminates at a second electrical connector 51 mounted on top of the second standoff 48. The connectors 46 and 51 permit the probe assembly 10 to be removably connected to the processing circuit.

A first pressure seal or O-ring 52 is position in a groove between the first connector standoff 42 and the first connector 46. Similarly, a second pressure seal or O-ring 53 is positioned in a groove between the second standoff 48 and the second connector 51. The pressure seals 52 and 53 isolate the relatively high fluid pressure in the flow passage 19 from the external atmosphere. Preferably, first and second electrical isolation sleeves 54 and 56 are provided, the first between the standoff 42 and the wire 38, and the second between the standoff 48 and the wire 40, to electrically insulate the wires from the standoffs. The standoffs 42 and 48 also isolate the electrical connectors 46 and 51 from the cryogenic temperatures of the two-phase fluids flowing through the flow directing tube 16.

Each of the standoffs 42 and 48 includes a pressure transducer port 57 and 58, respectively, which permits attachment of first and second pressure transducers 59 and 60, respectively, for monitoring the flow stream pressure at both ends of the flow directing tube 16. As will be discussed in greater detail below in conjunction with FIGS. 3 and 4, pressure fluctuations in the flow stream can create errors in the quality and flow measurements, but the processing circuit can compensate for these if it continually monitors the pressure at both ends of the flow directing tube 16.

The temperature of the flow stream also has an effect on the quality and flow measurements. For this reason, first and second thermocouples 62 and 64 are positioned in the flow passage 19 at the first and second ends 44 and 50, respectively, of the flow directing tube 16. Again, as will be discussed in greater detail below in conjunction with FIGS. 3 and 4, the temperature measurements provided by the thermocouples 62 and 64 can be employed by the processing circuit to compensate for the temperature induced measurement errors.

The foregoing arrangement of the probe assembly 10 results in the formation of first and second coaxial sensor capacitors 70 and 72 which are spaced from one another by the insulating sleeve spacer 24. The outer surface of the first probe 20 forms the inner plate of the first capacitor 70, while the outer surface of the second probe 22 forms the inner plate of the second capacitor 72. The outer plate for both capacitors is formed by the flow directing tube 16. The capacitance of each of the sensor capacitors 70 and 72 is directly proportional to the dielectric constant $\epsilon$ of the material disposed between the capacitor plates. In the probe assembly 10, this material comprises the two-phase flow stream in the flow passage 19. Since the dielectric constant varies depending upon the relative proportions of gas and liquid in the flow stream, the capacitance of each of the capacitors 70 and 72 is thus also directly related to the ratio of liquid to gas in the flow stream, otherwise known as the quality of the flow.

The first equation used to arrive at the quality is given as follows:

$$\epsilon = \frac{C(\ln(D_i/D_o))}{2\pi L \epsilon_0},$$

where $\epsilon$ is the dielectric constant of the flow mixture, C is the measured capacitance, $D_o$ is the outside diameter of the probes 20 and 22, $D_i$ is the inside diameter of the flow directing tube 16, L is the length of each probe 20 or 22, and $\epsilon_o$ is the dielectric constant of free space or 2.249 E-13 faraday/inch.

Once $\epsilon$ has been calculated from the above equation, the ratio of the liquid volume to the total volume in the flow stream, otherwise known as quality, can be calculated from the following equation:

$$Q = (\epsilon_f - \epsilon)/\epsilon_f - \epsilon_g),$$

where $\epsilon_f$ is the known dielectric constant of the liquid in the flow stream, and $\epsilon_g$ is the known dielectric constant of the gas in the flow stream.

The probe assembly 10 can also be employed to measure the flow stream's mass flow velocity. This is accomplished by continually monitoring the capacitance of both of the capacitors 70 and 72, and then cross-correlating these values with one another to determine when similar portions of the flow stream pass by each of the capacitors 70 and 72. Since the distance between the two capacitors 70 and 72 is known, the flow rate can be easily calculated by dividing this distance by the elapsed time required for one portion of the flow stream to travel between the first and second capacitors 70 and 72. Obviously, if the flow stream is completely homogeneous, this technique will not work. However, it works well with any two-phase flow having a large liquid component and a smaller gas component comprising randomly spaced bubbles in the liquid. As bubbles pass between the plates of the first capacitor 70 and then the plates of the second capacitor 72, they will have the same detectable effect on the dielectric constants of the two capacitors, and the cross-correlations of the measured capacitances will provide an indication of the instants when this same portion of the flow first passes by one of the capacitors 70 or 72, and then the other.

Figure 2:
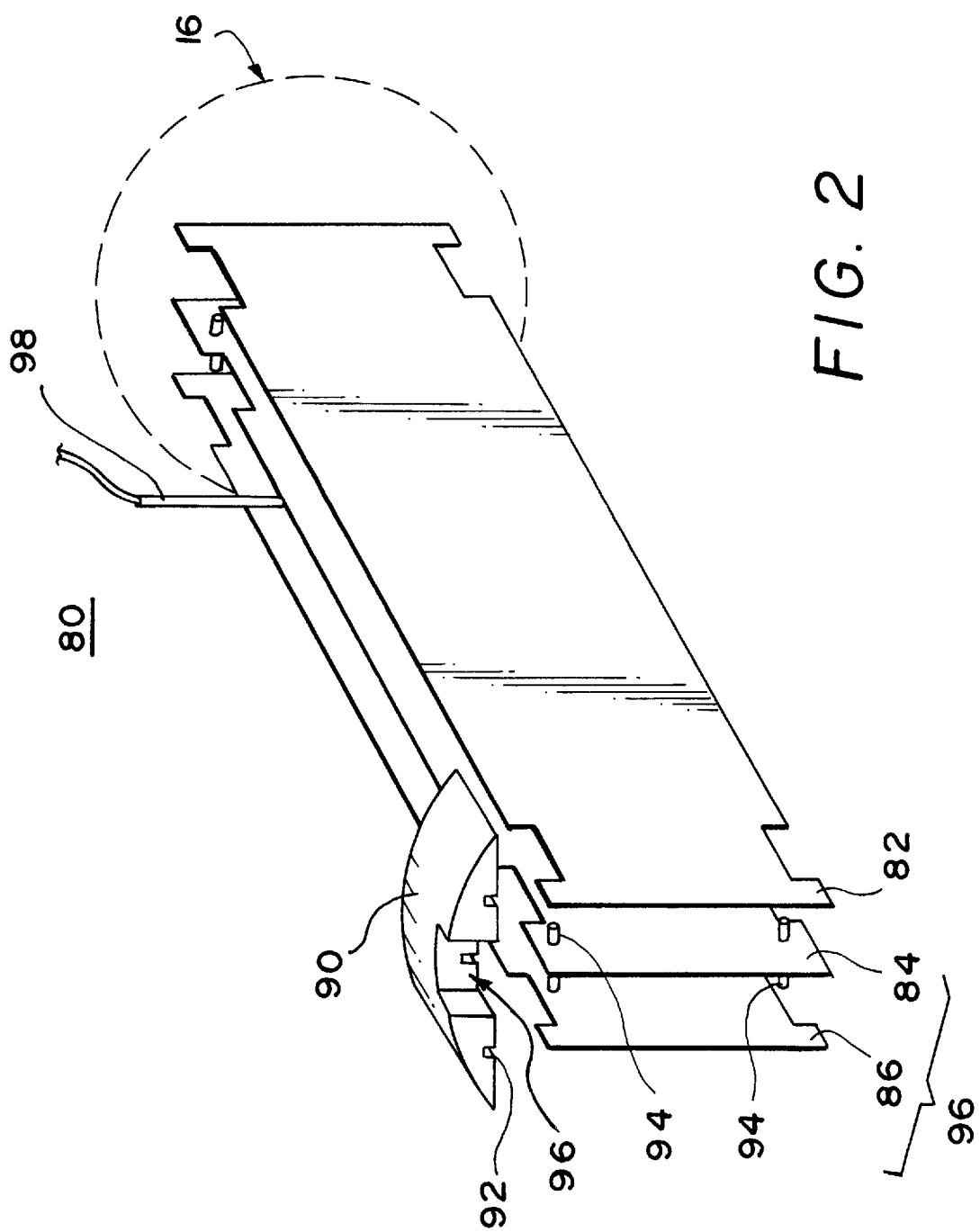
FIG. 2 is a perspective illustration of a second embodiment of a capacitance probe assembly for obtaining quality and flow measurements of a material flow stream.

FIG. 2 illustrates a second probe embodiment comprising a capacitive probe assembly 80 which includes first, second and third spaced, parallel plates 82, 84 and 86 that are positioned longitudinally in the flow directing tube 16. Four teflon blocks 90 (one shown) are provided which are designed to be press fit into the flow directing tube 16, and include a plurality of notches 92 for holding each of the plates 82, 84 and 86 in place. A plurality of pins 94 are secured at four locations in the center plate 84 which fit into an end notch 96 in each of the teflon blocks 90, and maintain the correct spacing between the center plate 84 and the outer plates 82 and 86.

The center plate 84 forms a first plate of a plate type sensor capacitor 96, while the outer plates 82 and 86 are grounded to one another, and thus together form the second plate of the capacitor 96. The reason that two ground plates are employed in the probe assembly 80 is to insure that the curvature of the tube 16 will not influence the measurements in a nonsymmetrical manner since the tube 16 is also at ground potential.

The probe assembly 80 differs from the probe assembly 10 illustrated in FIG. 1 in that it only uses a single sensor capacitor, and thus cannot be employed for making flow measurements, and also in that it employs a plate type capacitor instead of a coaxial capacitor. It will be understood, however, that it would be a simple matter to add yet another plate type capacitor to the assembly 80 which is spaced along the length of the tube 16 from the first capacitor 96, and thus enable the probe assembly 80 to be employed also for making flow measurements.

A stainless steel wire 98 is connected to the center plate 84 for applying a voltage thereto. As in the probe assembly 10 of FIG. 1, the wire 98 passes through a standoff to a connector for connection to the measurement circuitry. The standoff, connector and other external elements of the probe assembly 80 are the same as those elements employed in the probe assembly 10 of FIG. 1 and are thus not illustrated in FIG. 2. These also include the pressure transducers and thermocouples for monitoring pressure and temperature conditions within the flow stream, as well as the vacuum jacket arrangement for providing heat insulation to the flow stream.

Figure 3:
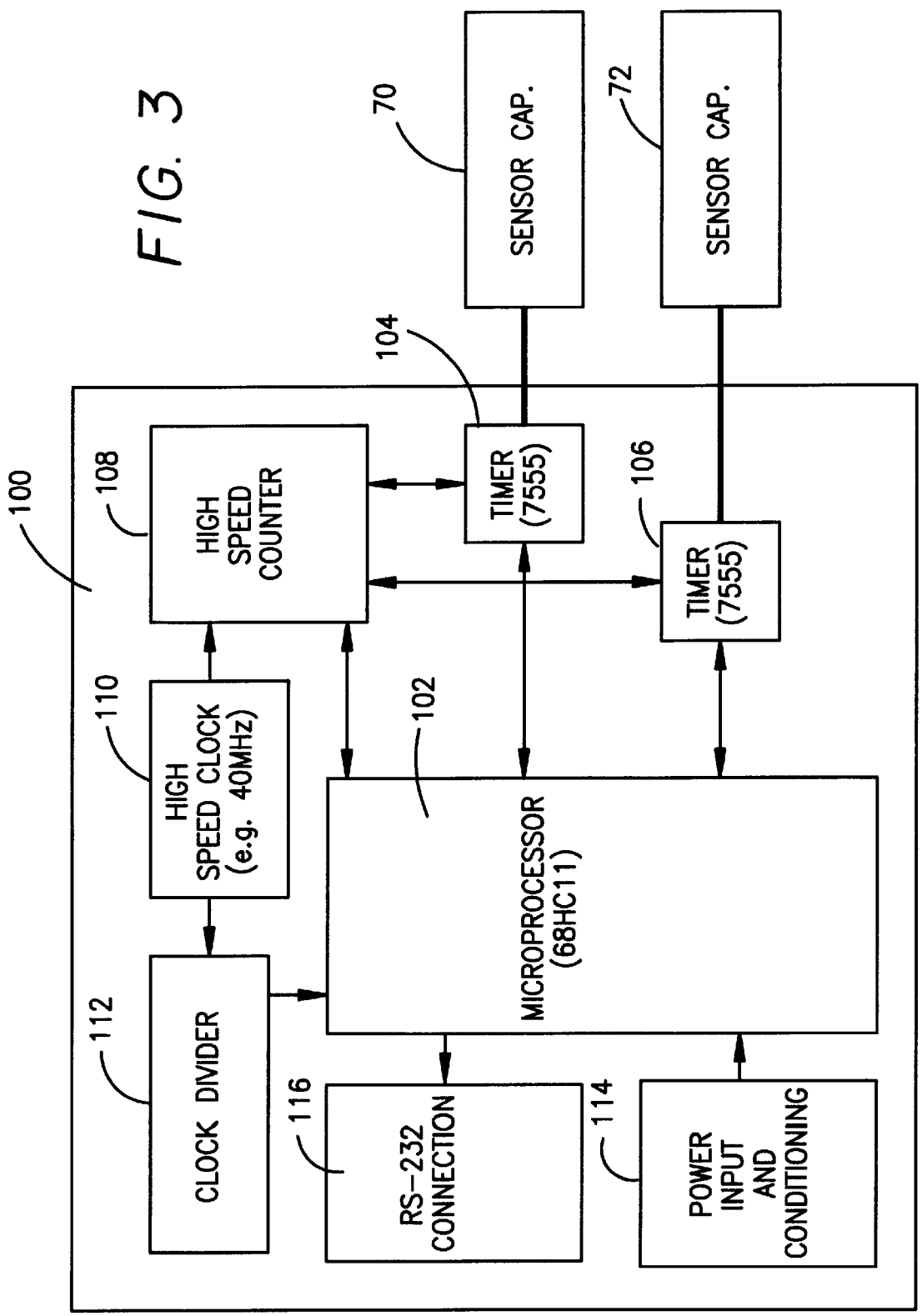
FIG. 3 is a general block diagram of a processing circuit for measuring the capacitance values of the sensor capacitors in the probe assembly of FIG. 1.

Turning now to FIG. 3, a general block diagram of a processing circuit 100 for measuring the capacitances of the probe sensor capacitors, from which the quality and flow rates of the flow stream can be determined, is illustrated. The circuit 100 is specifically designed for use with the two capacitor probe assembly 10 of FIG. 1, although it will be understood that it could also be employed with a single capacitor probe assembly, such as the assembly 80 of FIG. 2, by simply deleting the circuitry for the second capacitor. The heart of the circuit 100 is a 68HC11 microprocessor-based microcontroller 102 which controls operation of the various other components of the circuit 100, and performs data processing functions to calculate the capacitance of the two sensor capacitors 70 and 72.

Each of the probe sensor capacitors 70 and 72 is connected to a respective one of first and second 7555 timer circuits 104 and 106. A high speed counter circuit 108, preferably a 74AS869 synchronous counter, controls the operation of each of the timer circuits 104 and 106. A high speed oscillator clock 110, which operates at a frequency of 40 MHz, for example, controls operation of the high speed counter 108 and a clock divider circuit 112 that generates the slower clock pulses (e.g., 8 MHz) required for operation of the microcontroller 102.

Other conventional circuitry is also interfaced to the microcontroller 102 including power input and conditioning circuitry 114 and an RS-232 interface 116 for serial communication to a data acquisition system (not shown).

Figure 4:
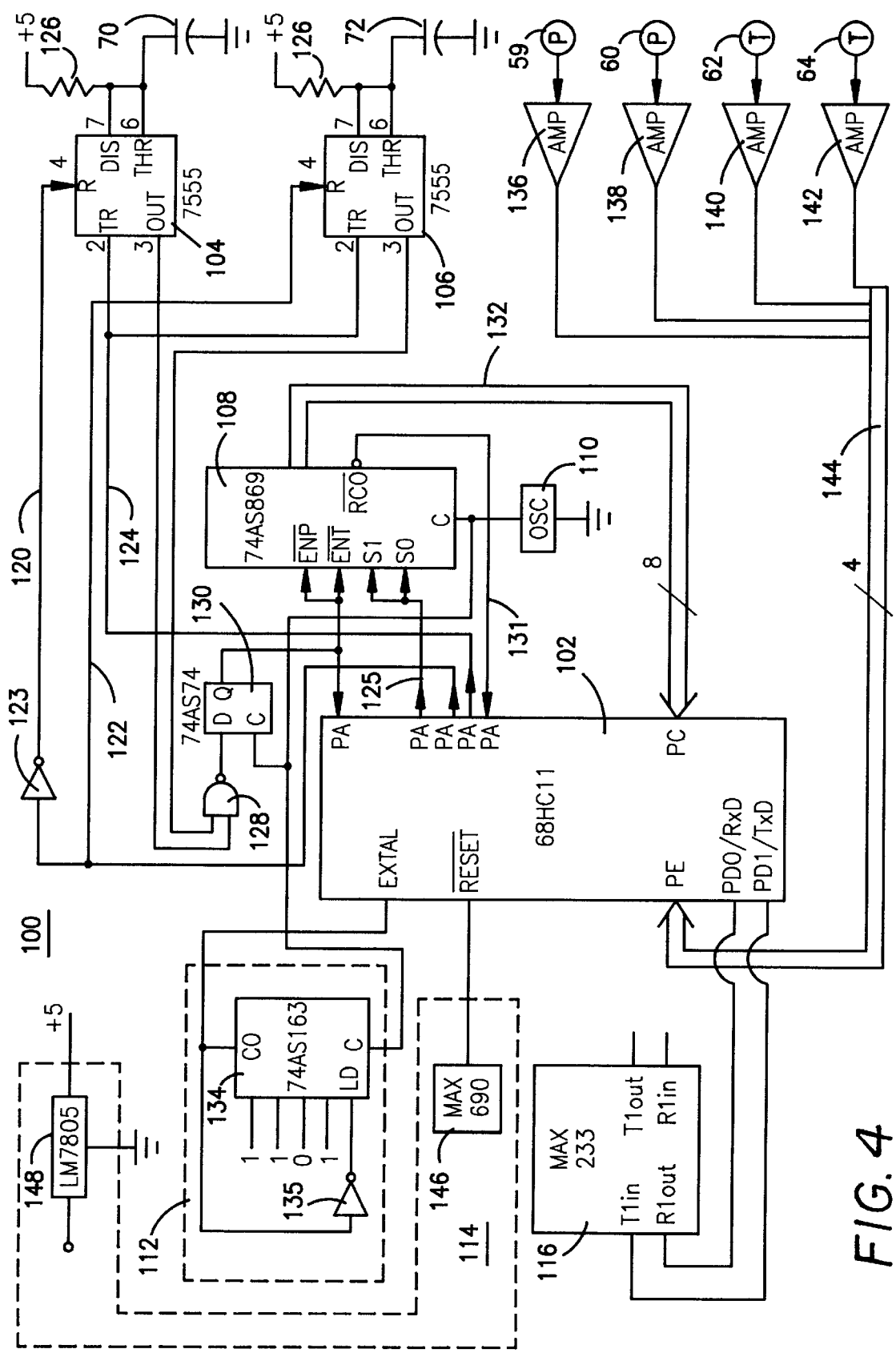
FIG. 4 is a detailed schematic circuit diagram of the processing circuit of FIG. 3.

The details of the processing circuit 100 are illustrated in FIG. 4. The 68HC11 microcontroller 102 sends complimentary signals from one of its PA I/O ports over first and second lines 120 and 122 to the reset inputs of the first and second 7555 timer circuits 104 and 106 to enable them one at a time to charge their respective capacitors 70 and 72. An inverter 123 is positioned in the line 120 going to the first timer circuit 104 to provide the complimentary signal thereto. The microcontroller 102 also sends a signal from another one of its PA I/O ports over a line 124 to the trigger inputs (pin 2) of the timer circuits 104 and 106 which causes the enabled one of the two to begin charging its respective capacitor. Simultaneously, the microcontroller 102 sends a signal from yet another one of its PA I/O ports over a line 125 to clear the count of the counter circuit 108, and cause it to start counting.

A large valued, e.g. 2 megohm, resistor 126 is connected between 5 volts and pins 6 and 7 (threshold and discharge, respectively) of each of the 7555 timer circuits 104 and 106. The sensor capacitors 70 and 72 are connected between these pins of their respective timer circuit 104 or 106, and ground. When the microcontroller 102 enables one or the other of the timer circuits 104 and 106 to begin charging their respective sensor capacitors 70 or 72, the discharge pin 7 of the enabled timer circuit 104 or 106 is allowed to float, thus allowing a charging current to pass through the resistor 126. The value of the resistor 126 is chosen to be very high to insure that the charging current is very low so that the capacitors 70 and 72 will not be charged so rapidly that the charging interval cannot be measured. Each of the capacitors 70 and 72 is charged to a threshold voltage which is preset in each of the timer circuits 104 and 106. Typically, this voltage is selected to be approximately two-thirds of the power supply voltage (5 volts), so that the charging current remains fairly constant throughout the charging interval. Assuming typical capacitance values for the sensor capacitors 70 and 72 on the order of 50 pF, the charging interval is on the order of 0.2 to 0.3 milliseconds, and a complete measurement can be made by the processing circuit 100 in approximately one millisecond or less.

Once the capacitor 70 or 72 is charged to the preset threshold voltage which is sensed by the respective timer circuit 104 or 106 on the threshold pin 6, the timer circuit 104 or 106 applies a zero voltage (binary zero) pulse on the discharge pin 7 to discharge the capacitor 70 or 72, and also on the output pin 3. The output pin 3 is connected through a NAND gate 128 to the input of a D-type 74AS74 flip flop 130. The flip flop 130 is controlled through its clock input by the high speed clock oscillator 110 which clocks the flip flop's input out its Q output. The Q output is fed to another one of the PA I/O ports of the microcontroller 102 to inform it that the capacitor charging has been completed. In addition, the flip flop's Q output is also fed to a pair of enable inputs ENP and ENT of the high speed counter circuit 108 to cause the counter circuit 108 to stop counting. Through a line 131 connected to another one of the PA I/O ports, the microcontroller 102 monitors the rollover output RCO from the counter 108 to keep track of how many times the counter 108 cycles during the measurement interval, and this internal counting is carried out to at least 8 bits of resolution. In addition, the eight bit count of the counter 108 is fed through an eight bit data bus 132 to the PC inputs of the microcontroller 102. The microcontroller 102 is thus provided with a very high resolution (at least 16 bits) digital representation of the measurement interval, and does so without the need for an A/D converter.

The divider circuitry 112 is preferably implemented using a 74AS163 synchronous binary counter 134 that is connected so that it generates one output pulse to the EXTAL clock input of the microcontroller 102 for every five input pulses received from the 40 MHz clock oscillator 110 so that the microcontroller 102 is driven by a clock frequency of 8 MHz. This is accomplished by permanently setting the four binary inputs of the counter 134 to 1011. The carry output CO of the counter 134 is also fed through an inverter 135 to control the load LD input of the counter 134. Thus, each time the counter transitions from 1111 to 0000, a CO pulse is generated which reloads 1011 into the counter 134 on the next clock pulse. The counter 134 then counts up through 1100, 1101, 1110, 1111 and finally to 0000 once again when the next CO pulse is generated.

The analog signals generated by each of the pressure transducers 59 and 60, and each of the thermocouples 62 and 64, are each first conditioned (e.g. amplified) in one of four corresponding op-amp based amplifier circuits 136, 138, 140 and 142. The analog outputs from the four amplifier circuits 136, 138, 140 and 142 are then fed through a four wire bus 144 to the analog PE inputs of the microcontroller 102 which utilizes the temperature and pressure measurement information to compensate for any temperature or pressure induced errors in the quality or flow measurements.

The remaining circuitry illustrated in FIG. 4 comprises the power input and conditioning circuitry 114 which includes a MAX690 watchdog circuit 146 and three (only one shown) LM7805 power supply circuits 148, one for each of the timer circuits 104 and 106, and the other for the remaining circuit components. Finally, the RS-232 interface 116 preferably comprises a MAX233 interface chip which is connected to the PD0/RxD and PD1/TxD ports of the microcontroller 102. Preferably, the microcontroller 102 obtains a plurality, e.g. four, of time interval measurements from the counter circuit 108 for each of the capacitors 70 and 72, and then averages these, before sending the measurement information through the interface 116. This is done simply to avoid sending an unmanageable amount of data through the interface 116.

The time interval count generated by the counter circuit 108 is linearly proportional to the capacitance value of the capacitor 70 or 72. The capacitance is in turn directly proportional to the dielectric constant of the flow stream, and this is proportional to the flow stream's quality. One way to calibrate the microcontroller 102 is to first measure the capacitance of one of the sensor capacitors 70 or 72 when the flow stream is entirely gas, and then measure the capacitance when the flow stream is entirely liquid. The value generated by the counter circuit 108 for the first measurement thus represents zero quality, while the count generated for the second measurement represents 100 percent quality, and these two counts can be employed to make zero and span adjustments in the microcontroller's software.

In summary, the present invention provides a combination quality and flow meter which employs both a capacitance probe assembly and a digital processing circuit for measuring the probe assembly's capacitance which result in a quality and flow measuring device that can make very fast, accurate, noise resistant measurements without requiring complex or expensive components.

Although the present invention has been disclosed in terms of a number of preferred embodiments, and variations thereon, it will be understood that numerous other modifications and variations could be made thereto without departing from the scope of the invention as defined in the following claims.

What is claimed is:

1. An apparatus for measuring characteristics of a flow stream comprising:
   a) a probe assembly including:
      i) a flow directing tube having a flow passage disposed therein for reception of said flow stream; and
      ii) at least a first sensor capacitor disposed in said flow directing tube, said sensor capacitor comprising first and second outer electrodes and a center electrode disposed longitudinally in said flow directing tube, each of said electrodes being parallel to and spaced from one another, said center electrode forming a first electrode of said sensor capacitor, and said first and second outer electrodes forming a second, ground electrode for said sensor capacitor; and
   b) a processing circuit for measuring the capacitance of said sensor capacitor, said processing circuit including:
      i) a digital counter circuit;
      ii) a clock oscillator for driving said digital counter circuit;
      iii) charging means for supplying a charging current to said sensor capacitor;
      iv) means for signalling simultaneously said counter circuit to begin counting and said charging means to begin supplying a charging current to said sensor capacitor;
      v) means for sensing when the voltage across said sensor capacitor exceeds a threshold voltage and generating a control signal in response thereto for signalling said counter circuit to stop counting; and
      vi) means for reading a counter value in said counter circuit, and determining the capacitance of said sensor capacitor therefrom.

2. The apparatus of claim 1, wherein said probe assembly further comprises a second sensor capacitor disposed in said flow stream, and spaced from said first sensor capacitor, and said processing circuit further includes:
   vii) second charging means for supplying a charging current to said second sensor capacitor in response to a signal from said means for signalling; and
   viii) second means for sensing when the voltage across said second sensor capacitor exceeds a threshold voltage and generating a control signal in response thereto for signalling said counter circuit to stop counting.

3. The apparatus of claim 2, wherein said processing circuit further includes means for periodically determining the capacitance values of said first and second sensor capacitors, and means for determining the flow rate of said flow stream from said capacitance values.

4. The apparatus of claim 1, wherein said flow stream is two-phase including a liquid component and a gas component, and said processing circuit further includes means for determining the volume ratio of said liquid component to the total volume of said liquid and gas components from the determined capacitance of said sensor capacitor.

5. The apparatus of claim 1, wherein said digital counter circuit further comprises:
   1) a high speed digital counter circuit with multiple bit resolution, said high speed digital counter circuit including a rollover output; and
   2) a microcontroller connected to said rollover output for monitoring the cycling of said high speed digital counter circuit and providing additional bits of resolution, wherein said high speed digital counter circuit and said microcontroller combine to provide a counter output having a higher number of bits of resolution than the number of bits of resolution of the high speed digital counter circuit.

6. An apparatus for measuring characteristics of a flow stream comprising:
   a) a probe assembly including:
      i) a flow directing tube having a flow passage disposed therein for reception of said flow stream; and
      ii) a sensor capacitor comprising first and second outer electrodes and a center electrode disposed longitudinally in said flow directing tube, each of said electrodes being parallel to and spaced from one another, said center electrode forming a first electrode of said sensor capacitor, and said first and second outer electrodes forming a second, ground electrode for said sensor capacitor; and
   b) a processing circuit for measuring the capacitance of said sensor capacitor to determine characteristics of said flow stream.

7. The apparatus of claim 6, wherein said probe assembly further comprises a vacuum jacket surrounding said flow directing tube for thermally insulating said flow directing tube.

8. The apparatus of claim 6, wherein said probe assembly further comprises temperature sensing means for sensing the temperature of said flow stream in said flow directing tube, and pressure sensing means for sensing the pressure of said flow stream in said flow directing tube.

* * * * *